(12) United States Patent
Bouillet et al.

(10) Patent No.: US 11,583,440 B2
(45) Date of Patent: Feb. 21, 2023

(54) TIP, INSERTER ATTACHMENT AND DELIVERY DEVICE

(71) Applicant: Pixium Vision SA, Paris (FR)

(72) Inventors: Elodie Bouillet, Paris (FR); Martin Deterre, Paris (FR); Yves Ruffieux, St-Aubin (CH); Hans Bernhard, Liebefled (CH)

(73) Assignee: Pixium Vision SA, Paris (FR)

( * ) Notice: Subject to any disclaimer, the term of this patent is extended or adjusted under 35 U.S.C. 154(b) by 329 days.

(21) Appl. No.: 16/650,465

(22) PCT Filed: Sep. 26, 2018

(86) PCT No.: PCT/EP2018/076196
§ 371 (c)(1),
(2) Date: Mar. 25, 2020

(87) PCT Pub. No.: WO2019/063655
PCT Pub. Date: Apr. 4, 2019

(65) Prior Publication Data
US 2020/0222231 A1    Jul. 16, 2020

(30) Foreign Application Priority Data
Sep. 27, 2017 (EP) .................................. 17001597

(51) Int. Cl.
| | | |
|---|---|---|
| *A61F 9/00* | (2006.01) | |
| *A61B 17/34* | (2006.01) | |
| *A61N 1/05* | (2006.01) | |
| *A61N 1/36* | (2006.01) | |
| *A61F 9/08* | (2006.01) | |
| *A61F 9/007* | (2006.01) | |
| *A61B 17/00* | (2006.01) | |

(52) U.S. Cl.
CPC ........ *A61F 9/0008* (2013.01); *A61B 17/3468* (2013.01); *A61F 9/007* (2013.01); *A61F 9/08* (2013.01); *A61N 1/0543* (2013.01); *A61N 1/36046* (2013.01); *A61B 2017/00469* (2013.01)

(58) Field of Classification Search
CPC ...... A61B 17/3468; A61B 2017/00469; A61N 1/36046; A61N 1/0543; A61N 1/372; A61F 9/08; A61F 9/007; A61F 9/0008
See application file for complete search history.

(56) References Cited

U.S. PATENT DOCUMENTS

| | | |
|---|---|---|
| 5,024,223 A | 6/1991 | Chow |
| 6,280,449 B1 | 8/2001 | Blake |
| 6,761,724 B1 | 7/2004 | Zrenner |
| 2004/0039401 A1 | 2/2004 | Chow et al. |
| 2004/0082981 A1 | 4/2004 | Chow et al. |
| 2007/0239066 A1* | 10/2007 | Laham ............... A61B 17/3478 600/567 |
| 2009/0234366 A1 | 9/2009 | Tsai et al. |
| 2013/0218269 A1* | 8/2013 | Schachar .................. A61F 2/91 623/4.1 |
| 2016/0184085 A1 | 6/2016 | Schneider et al. |

* cited by examiner

*Primary Examiner* — Brenda C Bernardi
(74) *Attorney, Agent, or Firm* — Workman Nydegger (57) ABSTRACT

The present invention relates to a tip for use with delivery devices, particularly for use in implanting retinal implants into the retinal space of an eye. The tip includes a flexible envelope and an internal sliding member. Further, the invention relates to an inserter attachment and a delivery device including said tip.

16 Claims, 6 Drawing Sheets

TIP, INSERTER ATTACHMENT AND DELIVERY DEVICE

There exists a variety of different diseases of the retina that are caused by a degeneration of the photosensitive cells of the retina. Examples of degenerative diseases are age-related macular disease (AMD) and retinitis pigmentosa (RP) are major causes of blindness, especially among the elderly worldwide. Both diseases are degenerative and associated with a loss of the photoreceptive cells (photoreceptors) of the retina. AMD causes loss of central vision, while RP initially causes gradual loss of peripheral vision, followed by loss of central vision resulting in complete blindness.

The retina is a light-sensitive layer at the back of the eye that includes almost one hundred thousand photoreceptor cells called rods and cones, which have the task of converting the energy from incident light into a nerve signal that is transmitted via the optic nerve to the visual cortex of the brain. Degeneration of the photoreceptor cells in AMD and RD progressively renders the retina less sensitive to light, and ultimately causes loss of sight. Importantly, the neural cells of the retina and the optic nerve are not affected as severely by the disease as the photoreceptor cells. Hence, there is still an intact and viable connection between the retina and the brain, which can be exploited for restoring vision.

Visual prosthesis systems comprising a retina implant have been developed which are helpful tools for at least partially re-establishing a modest visual perception and a sense of orientation for blind and visually impaired users by exploiting said fact that although parts of the retinal tissue have degenerated most of the retina may remain intact and may still be stimulated directly by light dependent electrical stimuli. Typically, retina implant is implanted into the patient's eye, effecting electrical excitation of the remaining neuronal cells upon light stimulation. When being stimulated, these remaining neuronal cells convey the artificially induced electrical impulses to the visual part of the brain through the optic nerve.

Retinal implants can be broadly divided into two categories: epi- and sub-retinal (Lin et al., 2015, Retinal prostheses in degenerative retinal diseases, J Chin Med Assoc.; 78(9): 501-5). Epi-retinal devices are placed on or near the inner surface of the retina, i.e. the side of the retina which is first exposed to incident light and along which the nerve fibers of the ganglion cells pass on their way to the optic nerve. Epi-retinal implants typically comprise a chip with a plurality of pixel elements capable of receiving an image projected by an extraocular device (typically a camera and a microelectronic circuit for decoding incident light) on the retina through the lens of the eye, for converting the image into electrical signals and for further conveying the signals into electrical stimuli via a plurality of stimulation electrodes to stimulate the retinal cells adjacent the chip, in order to reconstruct or improve vision of blind or partially blind patients. In contrast, sub-retinal devices are placed under the retina, between the retina and the underlying retinal pigment epithelium or other deeper tissues.

More recently, so-called sub-retinal implants have been proposed. In particular, Chow et al. have described various designs for implants to be inserted in the sub-retinal space, i.e., a space created between the inner and outer retinal layers, in U.S. Pat. Nos. 5,016,633; 5,024,223; 5,397,350; 5,556,423; 5,895,415; 6,230,057; 6,389,317, 6,427,087. WO2016180517, WO2016206809, WO2016180535, WO2017045756 and EP17181558.2. Generally, the implants described in these patents are placed in contact with the photoreceptor layer of the inner retina such that electrodes on the implants can provide stimulating currents, derived from the photovoltaic conversion of incident light, to the inner retina.

Additionally, techniques and devices for inserting such implants into the sub-retinal space are also described in various ones of these patents, e.g., U.S. Pat. Nos. 5,016,633; 5,024,223 and 6,389,317. While some of these techniques and, more particularly, devices, have been used to deliver implants in the past, several problems persist. Electrostimulatory implants, in particular retinal implants, are very thin and brittle, and exhibit a low mechanical stress resistance. Such implants can get readily jammed between complex mechanical parts of commonly used delivery devices, leading to damage of the implant. Thus, there still exists a need for improved techniques and devices to further simplify delivery of implants, particularly retinal implants.

It is the object of the present invention to comply with this need.

Although the present invention is described in detail below, it is to be understood that this invention is not limited to the particular methodologies, protocols and reagents described herein as these may vary. It is also to be understood that the terminology used herein is not intended to limit the scope of the present invention which will be limited only by the appended claims. Unless defined otherwise, all technical and scientific terms used herein have the same meanings as commonly understood by one of ordinary skill in the art.

In the following, the features of the present invention will be described. These features are described for specific embodiments. It should, however, be understood that they may be combined in any manner and in any number to generate additional embodiments. The variously described examples and preferred embodiments should not be construed to limit the present invention to only explicitly described embodiments. This present description should be understood to support and encompass embodiments, which combine the explicitly described embodiments with any number of the disclosed and/or preferred features. Furthermore, any permutations and combinations of all described features in this application shall be considered supported by the description of the present application, unless it is understood otherwise.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of". The term "comprising" thus encompasses "including" as well as "consisting" e.g., a composition "comprising" X may consist exclusively of X or may include something additional e.g., X+Y.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

The word "substantially" does not exclude "completely" e.g., a composition which is "substantially free" from Y may be completely free from Y. Where necessary, the word "substantially" may be omitted from the definition of the invention.

The term "about" in relation to a numerical value x means x±10%.

The present invention provides a tip, an inserter attachment and a delivery device comprising said inserter attachment. In a first aspect, the invention relates to a tip 100 for a delivery device, said tip comprising a flexible envelope 101, said envelope 101 surrounding or defining a lumen 104. Envelope 101 may preferably enclose lumen 104, forming a rounded or flattened tube. However, it is envisaged that envelope 101 preferably comprises at least one opening at its distal and proximal end.

The inventive tip is specifically envisaged for use with delivery devices capable of delivery of an implant to a body site of interest. Thus, the term "delivery device" as used herein preferably refers to devices configured to deliver implants, preferably retinal implants, to a body site of interest. Such devices may also be referred to as "implant delivery devices". Preferably, said implant may be a retinal implant, e.g. a sub-retinal or epi-retinal implant, and the tip may preferably be configured to deliver said retinal implant to the (human) eye. To that end, the tip may take any suitable shape. E.g., the tip may be curved or straight. It may be preferred that the tip 100 has a curved shape. The shape of tip 100 may vary along its length. Accordingly, tip 100 may comprise curved or straight portions or both, depending on the desired site of delivery within the body.

Flexible envelope 101 may preferably comprise or consist of at least one flexible and preferably biocompatible material. It may be preferred that said material is sterilisable. Suitable, preferred materials may be selected from polytetrafluorethylene PTFE; polytetrafluorethylene (PTFE); polyurethane, polyethylene, vinyl, expanded-polytetrafluoroethylene (ePTFE); silicone; as well as fluorinated ethylene propylene FEP, or any other biocompatible polymers such as polyvinyl chloride PVC, polycarbonate PC, polypropylene PP, polyethylene PE, polyimide PI, acrylonitrile butadiene styrene ABS; or other materials. Envelope 101 may further advantageously be transparent or translucent in order to allow the user to control the position of the internal sliding member and the implant within the tip upon implantation. It is conceivable that envelope 101 may comprise one or several layers, which are preferably composed of flexible materials as exemplified herein. Envelope 101 may preferably have a (total) wall thickness of about 0.1 mm, 0.2 mm, 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3 mm or more., more preferably of between about 0.2 mm and 1.2 mm, even more preferably of between about 0.4 mm and 0.8 mm. In some embodiments, envelope 101 may have a (total) wall thickness of about 0.5 mm.

The skilled person will be readily able to choose an appropriate material and (total) wall thickness which ensures sufficient stability while at the same time providing the required flexibility.

Flexible envelope 101 surrounds and thereby defines lumen 104, which is preferably characterized by a dilatable cross-section. Flexible envelope 101 (and preferably lumen 104) is preferably capable of conforming to the shape of an internal sliding member 102 passing through lumen 104.

Internal sliding member or pusher 102 is preferably movably disposed within lumen 104 and is preferably capable of moving in longitudinal direction along the length of lumen 104. Internal sliding member 102 is preferably capable of engaging with and pushing implant 600 which is initially retained in lumen 104. Preferably, upon actuation by suitable actuation means, internal sliding member 102 thus preferably pushes implant 600 out of lumen 104 for delivery to the body site of interest (e.g. the eye). Internal sliding member 102 may preferably be composed of a material which is rigid enough to deform lumen 104 of envelope 101 and push implant 600 disposed within lumen 104. Said material may further preferably be sterilisable. Preferably, internal sliding member 102 may be composed of a suitable metal, e.g. stainless steel, anodized aluminium, an aluminum alloy, a titanium alloy, nitinol, or any other preferably biocompatible metal.

Internal sliding member 102 preferably exhibits dimensions exceeding the dimensions of the dilatable cross-section of lumen 104 when in an un-dilated state. Upon actuation, internal sliding member 102 preferably travels through and thereby deforms lumen 104 such that the dilatable cross-section essentially corresponds to the dimensions of internal sliding member 102. The dilatable cross-section now preferably exceeds the dimensions of the implant 600 retained within lumen 104, such that implant 600 can be pushed by internal sliding member 102 to travel longitudinally along lumen 104.

Accordingly, internal sliding member 102 preferably occupies the dilated cross-section of lumen 104 in its entirety, such that there is no gap between internal sliding member 102 and the inner surface of envelope 101. Thereby, implant 600 engaging with and being pushed by internal sliding member 102 through (dilated) lumen 104 is preferably prevented from being stuck or jammed between internal sliding member 102 and the internal surface of envelope 101. Furthermore, there is preferably only one contact point between implant 600 and internal sliding member 102, whereas the remaining surfaces and edges of implant 600 preferably only contact flexible envelope 101. Thereby, mechanical stress on the rigid and sensible implant 600 is preferably minimized.

Lumen 104 is characterized by a dilatable cross-section. The cross-section may be rounded or flattened. Optionally, the shape of the cross-section may vary along the length of tip 100. Lumen 104 may thus exhibit both rounded and flattened portions. The cross-section may exhibit a dilatable diameter or a dilatable width and/or height. Lumen 104 is preferably capable of conforming to the shape of an internal sliding member 102 passing through. More preferably, the dilatable cross-section of lumen 104 is preferably dilated by passing through of internal sliding member 102 within lumen 104.

The dimensions (i.e., diameter, height or width) of the dilatable cross-section may preferably be chosen such that implant 600 is secured or retained within lumen 104 when in an un-dilated state. Preferably, in an un-dilated state, the dilatable diameter or width of lumen 104 essentially corresponds to the width of implant 600, such that implant 600 is retained within lumen 104, thereby preventing premature release and/or damage to implant 600. Preferred implants in the context of the present invention include, without limitation, the retinal implants described in WO2016180517, WO2016206809, WO2016180535, WO2017045756 or EP17181558.2. Such implants typically have a width of at least about 1 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, preferably of between about 1.5 mm and 2.0 mm. The dimensions of the dilatable cross-section are thus preferably chosen to hold implant 600 in place until actuation of and dilation by internal sliding member 102. Thus, the dilatable cross-section may preferably exhibit a dilatable width or diameter of at least about 1 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, preferably of between about 1.5 mm and 2.0 mm, depending on the width of the implant. Additionally or alternatively, lumen 104 may exhibit a dilatable height of at least about 0.1 mm, 0.2 mm, 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm or more. The dimensions of lumen 104 may optionally be dilatable by at least 1%, 2%, 3%, 4%, 5%, 6%, 7%, 8%, 9%, 10%, 11%, 12%, 13%, 14%, 15%, 16%, 17%, 18%, 19%, 20% or more.

The dilatable cross-section (preferably characterized by a dilatable diameter, height and/or width) of lumen 104 is preferably chosen to (in its un-dilated state) fall below the dimensions of internal sliding member 102. Preferably, said dilatable cross-section is dilatable to conform to the dimensions of internal sliding member 102. Upon actuation and movement of internal sliding member 102, lumen 104 is preferably dilated to essentially correspond to the dimensions of internal sliding member 102. Thereby, internal sliding member 102 is preferably capable of proceeding along the length of lumen 104. Internal sliding member 102 may preferably engage with implant 600 retained within lumen 104, and, upon actuation and dilation of lumen 104, eventually pushes implant 600 from opening 103 at the distal end of tip 100.

Depending on the flexibility of envelope 101, the skilled person will be readily able to determine the dimensions of the dilatable cross-section that are necessary to ensure that implant 600 is held in place when the internal sliding member is not actuated, but can be dilated to reach dimensions allowing internal sliding member 102 optionally pushing implant 600 to travel along the length of the tip in a longitudinal direction. Internal sliding member 102 may deform lumen 104 laterally or horizontally or both. Accordingly, lumen 104 may exhibit a dilated diameter or width of at least about 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm as internal sliding member 102 passes through, depending on the dimensions of internal sliding member 102. Additionally or alternatively, lumen 104 may exhibit a dilated height of at least about 0.15 mm, 0.2 mm, 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm or more as internal sliding member 102 passes through, depending on the dimensions of internal sliding member 102.

The inventive tip comprises a distal end, a longitudinal portion and a proximal end. The proximal end is preferably configured to be (optionally detachably) affixed to or mounted on a delivery device. The longitudinal portion preferably retains implant 600 and internal sliding member 102. The longitudinal portion is of sufficient length to allow the tip 100 to be inserted intraocularly and positioned in close proximity to the retina, or even sub-retinally, when being manipulated externally via the handpiece 301. The distal end (or "free end") is preferably configured for insertion into a body site of interest and delivery of implant 600 to said body site. The distal end may be rounded or flattened and optionally tapered. The distal end preferably comprises opening 103 for releasing implant 600 to the body site of interest, e.g. the (human) eye. Opening 103 is thus preferably configured to allow implant 600 and optionally internal sliding member 102 to pass through. In order to preferably avoid damage to tissue upon insertion and implant delivery, tip 100 and in particular its free end may comprise rounded edges.

Tip 100 may comprise in implant 600, which is preferably a retinal implant, retained or secured in lumen 104. Retinal implants particularly envisaged for delivery include the implants described in WO2016180517, WO2016206809, WO2016180535, WO2017045756 or EP17181558.2, each of which is incorporated herein by reference in its entirety.

In a further aspect, the invention relates to an inserter attachment 200 for an implant device, said inserter attachment comprising tip 100 as described herein, and optionally a cap 201 (detachably) affixed to tip 100. Inserter attachment 200 may further comprise suitable engagement means for affixing inserter attachment 200 to a delivery device 300.

In a further aspect, the invention relates to a cap 201 configured to be affixed to a tip 100 according to the invention, thereby preferably covering the distal end of tip 100 and optionally sealing opening 103. Cap 201 preferably comprises suitable engagement means for affixing cap 201 to the distal end of tip 100. Such engagement means may be selected from any means known in the art. In some embodiments, cap 201 may comprise a shaft corresponding to the shape and dimensions of the distal end of tip 100 such that the shaft can be slipped over distal end of tip 100 so as to seal opening 103 of the tip. Cap 201 is preferably removed immediately prior to delivery of implant 600 residing within lumen 104 of tip 100. Cap 201 may be composed of material suitable to cover tip 100 and optionally seal opening 103. Suitable materials may be selected from a materials that substantially retain their formed shape (i.e., a memory material), but that are relatively compliant, such as so-called shrink tubing; or low density polyethylene, e.g. PTFE; or polyether ether ketone (PEEK). The material may optionally be transparent or translucent. The inserter attachment 200 is preferably affixed to a delivery device as described herein. The present invention envisages the tip 100 or inserter attachment 200 to be removably (or detachably) or permanently affixed to delivery device 300.

In a further aspect, the invention relates to the use of tip 100 or inserter attachment 200 for assembling a delivery device.

In a further aspect, the invention relates to a delivery device 300 comprising a handpiece 301 with housing 302, engagement means 400, actuation means 500 and tip 100, said tip preferably forming part of inserter attachment 200.

Handpiece 301 preferably comprises three major systems, a housing system, an inserter attachment engagement system and an inserter attachment actuation system. The inserter attachment engagement system allows a user of the handpiece 301 to engage/disengage an inserter attachment to/from the handpiece. The inserter attachment actuation system functions to translate actuation of the lever 303 into movement of a internal sliding member 102 of the inserter attachment 200. Finally, the housing system serves to encase and substantially protect the inserter attachment engagement system and the inserter attachment actuation system.

Handpiece 301 may have a shape that is simple for constructions and/or a shape that is ergonomically formed to rest within a human hand. Handpiece 301 may be constructed of substantial stiffness to resist flexing during use by the user.

It may be preferred that all of the components forming the handpiece 301 and inserter attachment 200 are made from sterilizable materials. The constituent components of the handpiece 301 and optionally inserter attachment 200 may be fabricated from any combination of the following materials: stainless steel, anodized aluminium, titanium, polysulfone, Radel® (polyethersulfone), silicone, epoxy, Buna-N, lightweight molded plastic, e.g., polystyrene. In other embodiments, other injection molded plastics may be used such as polyurethane, polypropylene, high molecular weight polyurethane, polycarbonate or nylon. Alternatively, construction materials may include aluminum, stainless steel, a metal alloy or a composite material. In addition, housing 302 and lever 303 may be constructed of different materials instead of being constructed out of the same material. In some examples, housing 302 and/or lever 303 may include a rubber or soft tactile surface to increase the friction with a hand of the user and prevent the hand of the user from slipping during use. In some embodiments, housing 302 and lever 303 may be assembled through snap fit connections, adhesives or mechanical fixation devices such as pins or screws.

Generally, it is preferred that all components of the handpiece 301 and inserter attachment 200 be substantially free of sharp edges or corners, particularly any movable components or components that may come in contact with biological tissues. To this end, with respect to any metallic (e.g., stainless steel) components, it is preferred that such component be electropolished to minimize the generation of particulate matter that might otherwise result from the frictional engagement of various components.

Figure 1:
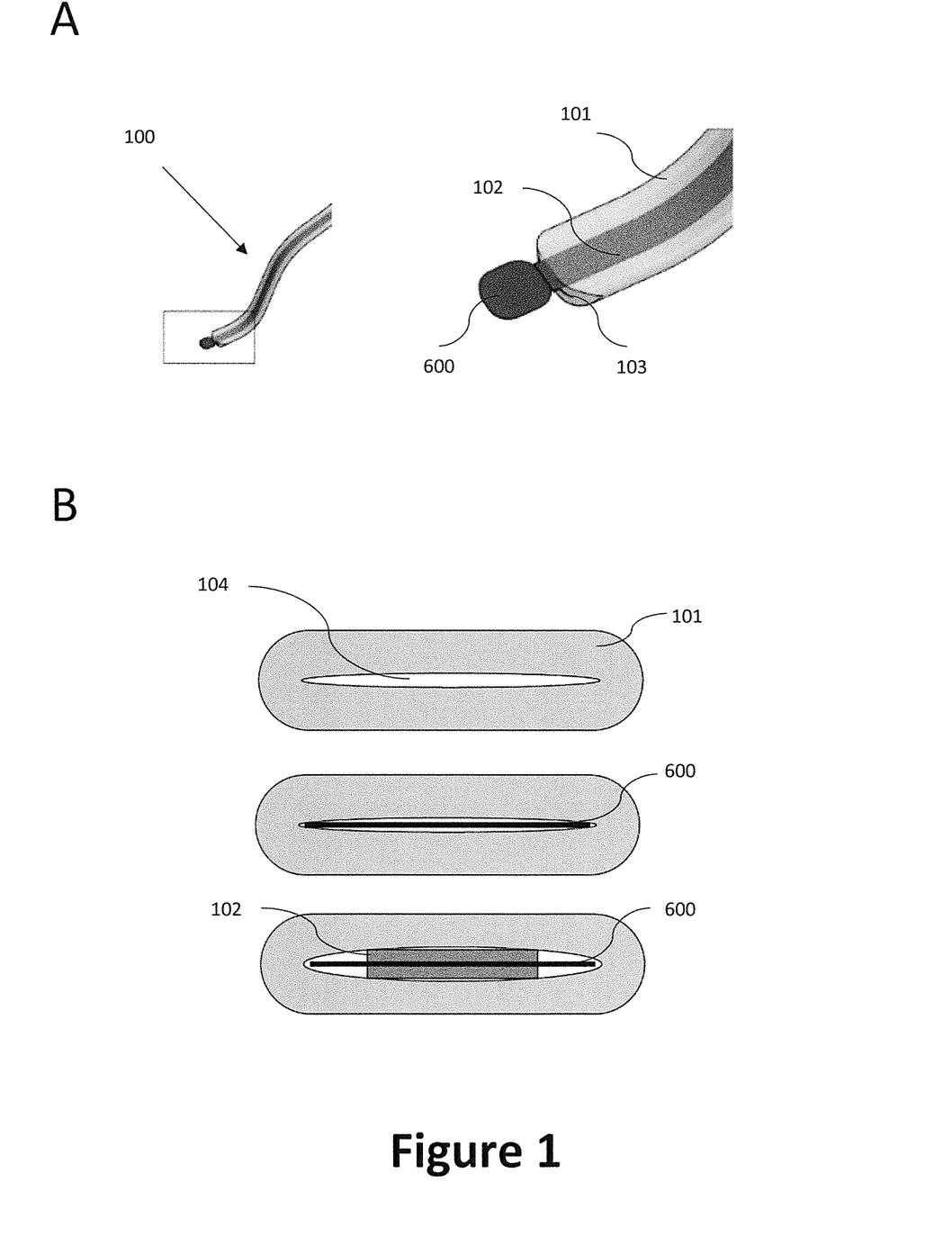
FIG. 1A illustrates release of implant 600 from tip 100 by the action of internal sliding member 102 engaging with implant 600. Left: Overview. Right: Enlargement.
FIG. 1B schematically shows the dilatable cross-section of lumen 104 without implant (top), retaining an implant 600 (middle) and with internal sliding member 120 engaging with implant 600 and deforming the lumen 104.
FIGS. 1C and 1D schematically show the dilatable cross-section of lumens 104 according to alternative embodiments without implant (top) and with internal sliding member 120 engaging with implant 600.

Although FIG. 1 and subsequent figures describe specific embodiments for the three major systems, those having ordinary skill in the art will recognize that various aspects of each system may be readily implemented using techniques other than those described in the instant specification.

Housing 301 may be substantially cylindrical, although that characteristic is not a requirement and virtually any cross-sectional area and/or exterior surface shape may be equally employed. Housing 301 may further comprise recesses such that an opening for the lever 303 is defined in the surface of housing 301.

Engagement means 400 are preferably configured to allow the engagement and optionally disengagement of tip 100 or inserter attachment 200 to/from handpiece 301. Tip 100 or inserter attachment 200 may thus be detachably or permanently affixed to handpiece 301 via suitable engagement means 400. It may be preferred that tip 100 or inserter attachment 200 may be permanently affixed to handpiece 301. The skilled person is readily able to provide suitable engagement means, e.g. threads, shafts, buttons, scews, nails bolts, studs or pins. In some embodiments, tip 100 or inserter attachment 200 are affixed to housing 302 via screws or bolts (401, 402). To prevent inadvertent movement of the lever 303, a slidable trigger lock or safety pin 304 may be provided.

Handpiece 301 further preferably comprises actuation means for controlling and driving the movement of internal sliding member 102 within lumen 104 of tip 100. Suitable actuation means are known in the art and may be chosen from a lever 303, or alternatively a plunger, a wheel, or any other suitable means. A spring 501 may translate the actuation of lever 303 to internal sliding member 102 within lumen 104 upon actuation of lever 303 by a user.

In a further aspect, the present invention relates to a method for manufacturing a tip or inserter attachment according to the invention, comprising providing an envelope as described herein; optionally providing an internal sliding member as defined herein; and affixing an internal sliding member to said envelope. In particular, the method may involve inserting said internal sliding member into said envelope.

Envelope 101 may preferably be made from post-processing of a (standard) circular tube. Preferably, a circular tube being basis for the envelope may be pressed, preferably to a predetermined height such that preferably a cross section of a lumen of the tube adapts to the above described desired or predetermined shape.

Pressing of the tube may preferably be performed at room temperature, or according to an alternative, the envelope may be formed by pressing a circular tube at an elevated temperature. If the tube comprises a polymer material, the elevated temperature may exceed a glass transition temperature of the polymer material. Preferably, the temperature applied to the tube is lowered, preferably below the glass transition temperature, particularly preferably to room temperature, before compression of the tube is released.

According to a preferred embodiment, a mandrel is inserted into the tube before pressing and wherein the mandrel is being kept inside the tube during the step of pressing the tube. Hence, the lumen of the envelope may adapt to a shape predetermined by the mandrel. After forming of the envelope, the mandrel is removed and the envelope may keep the given inner profile.

According to yet another embodiment, the envelope may be formed by extruding directly with the desired profile. Alternatively, the envelope may be formed by overmolding a suitable material around a mandrel, wherein preferably the mandrel comprises the shape of the desired profile of the lumen of the envelope. After forming of the envelope, the mandrel is removed and the envelope may keep the given inner profile.

The envelope may alternatively be formed by a heat shrink step, preferably, by forming a heat shrink tube around a mandrel, wherein the mandrel comprises the shape of the desired profile of the lumen of the envelope. After forming of the envelope, the mandrel is removed and the envelope may keep the given inner profile. With this method the tube may be made from standard heat shrink tube comprising a suitable material, for instance PTFE or FEP.

Preferably, the lumen comprises an oval cross-sectional shape, preferably having two opposing pointed corners. Alternatively, the lumen may comprise any other suitable cross-sectional shape, wherein preferably, the lumen comprises a section having a first height and at least one other section having a second height smaller than the first height. Preferably, the section having the first height provides a first cavity for receiving sliding member 102. The second section having the second height may be provided for holding, positioning and/or guiding implant 600.

The tip may preferably be made in one piece. Alternatively, the tip may comprise two or more parts assembled together. In the latter case, a distal region part of the tip in which the implant is received may be made of a polymer, preferably a flexible and transparent polymer, or any other suitable material listed above. The distal region part preferably comprises a lumen having a cross section as described above. One or more proximal parts may be provided adjacent to the distal region part in a proximal direction thereof, wherein the one or more proximal parts may extend proximal to the distal region part, and may comprise the same material as the distal region part, or may comprise a different material and/or a different profile, wherein preferably the proximal part may be a flattened rigid tube, preferably comprising a metal material. The distal region part and the one or more proximal parts may preferably be assembled by gluing or any other assembly method like welding or clipping or press-fitting.

In a further aspect, the present invention relates to a method of manufacturing or assembling a delivery device, comprising providing an inserter attachment 200; providing a handpiece 300 and affixing said inserter attachment 200 to said handpiece 301, optionally via suitable engagement means.

In yet a further aspect, the present invention relates to a method of delivering an implant to a body site of interest, said method making use of a delivery device according to the invention. The implant is preferably a retinal implant as described herein. The method may thus advantageously comprise inserting said implant into the interter attachment 200 of delivery device 300, inserting the free end of the tip into the body site of interest (e.g. the eye) and actuating lever 303 to push the internal sliding member 102 engaging with implant 600 to release the implant to the body site of interest.

DESCRIPTION OF THE FIGURES

FIG. 3B-C illustrate the function of inserter attachment 200 mounted on delivery device 300.

FIG. 4A is a cross-sectional view of delivery device 300 in an un-actuated state. Lever 303 is not actuated. Envelope 101 and internal sliding member 102 are affixed to housing 302 via fastening means 401, 402. Spring 501 is relaxed, holding internal sliding member 102 in a retracted position. FIG. 4B is a cross-sectional view of delivery device 300 in an actuated state. Lever 303 is actuated. Spring 501 is compressed, pushing internal sliding member 102 to travel longitudinally along lumen 104 towards the distal end of tip 100.

The inventive tip, inserter attachment and delivery device preferably have the following advantages:

The flexible envelope combined with a rigid pusher minimizes mechanical stress on the implant, as there is only one rigid contact point, while all other surfaces of the implant are in contact with flexible material.

The dimensions of the flexible envelope are chosen such that the implant is retained in the lumen and no accidental release can take place before actuation of the pusher.

By combining a pusher that is bigger than the lumen, the implant is prevented from being stuck or jammed between pusher and lumen upon actuation of the pusher.

Referring to the figures, FIG. 1A illustrates the curved longitudinal portion and proximal end of tip 100 with flexible envelope 101 surrounding internal sliding member 102 which, upon actuation, moves through the lumen 104 of flexible envelope 101 to engage with implant 600, eventually pushing implant 600 out of opening 103 at the distal end of tip 100. FIG. 1B shows the cross-section of tip 100. Flattened flexible envelope 101 defines or surrounds flattened lumen 104 characterized by a dilatable cross-section (top). The dimensions and in particular the width of the dilatable cross-section are chosen to essentially correspond to the width of implant 600 retained in lumen 104, thereby holding implant 600 in place when in an un-dilated state (middle). Upon actuation of internal sliding member 102, exhibiting dimensions exceeding the dimensions of the dilatable cross-section, lumen 104 is deformed. Internal sliding member 102 engages with implant 600 and is now capable of pushing implant 600 through dilated lumen 104.

Referring to FIG. 1C, a shows the cross-section of tip 100 according to another preferred embodiment. The envelope according 101 to this embodiment may be made by pressing a circular tube at a temperature above the glass transition temperature of the tube's material, wherein a mandrel was used for predefining the cross-sectional shape of lumen 104. Hence, lumen 104 comprises a central first cavity having a first height for receiving internal sliding member 102. In addition, lumen 104 comprises two opposing side cavities having a second height lower than the first height for receiving and guiding implant 600. FIG. 1D illustrates the cross-section of tip 100 according to yet another preferred embodiment. Lumen 104 comprises two sections comprising a reduced height. In this configuration implant 600 is held on its faces at the section with reduced height rather than on its edges. Again, internal sliding member 102 is received in a central cavity provided between the two sections with reduced height. The envelope 101 according to this embodiment may be manufactured by for instance by a heat shrink process of a tube around a mandrel.

Figure 2:
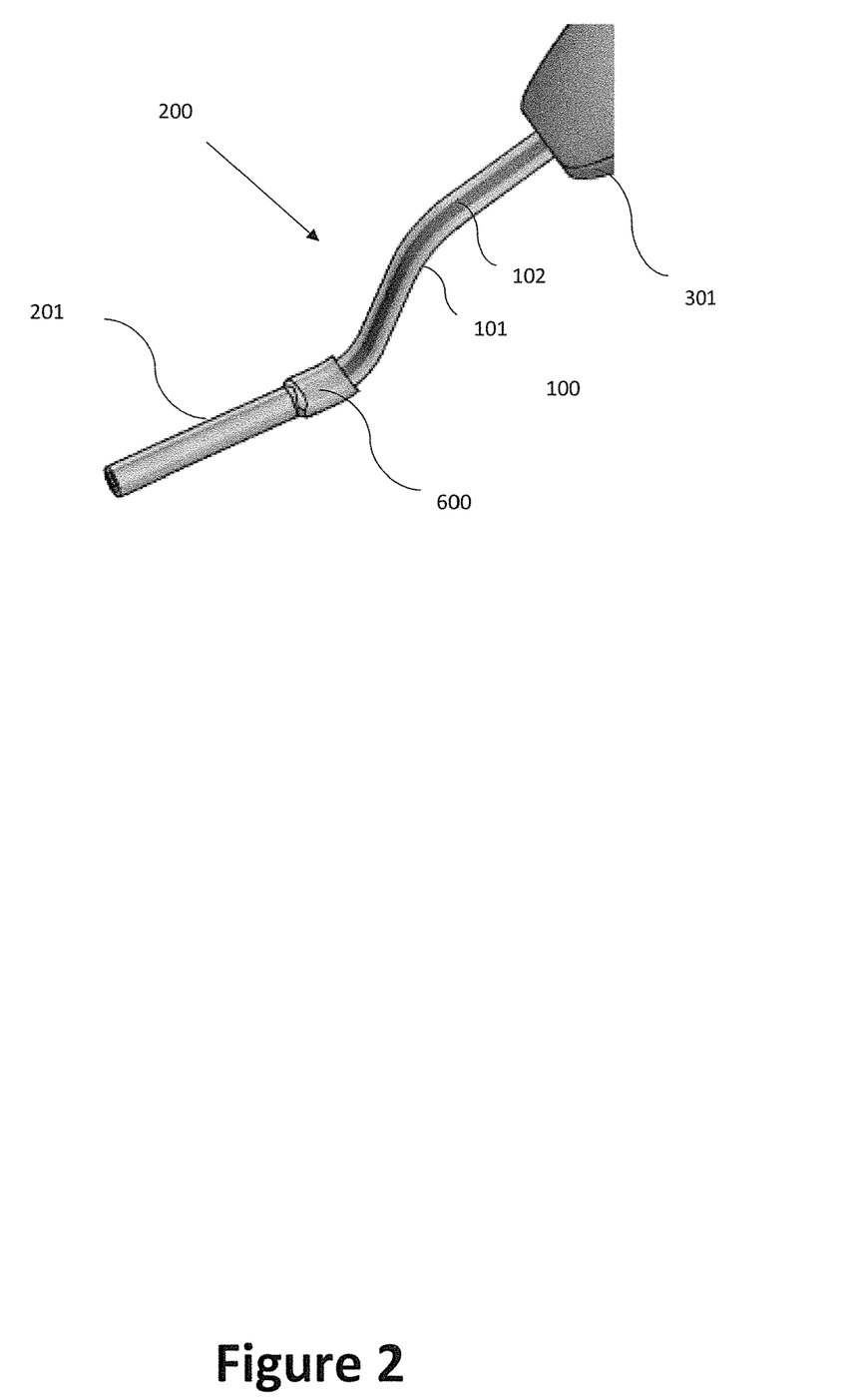
FIG. 2 shows an inserter attachment 200 with a cap 201 detachably affixed to tip 100.

FIG. 2 illustrates an inserter attachment 200 comprising a tip 100 mounted on delivery device 300. Cap 201 may optionally be attached to the distal end of tip 100 to cover the tip, optionally seal opening 103 and/or protect implant 600 residing in lumen 104 until delivery.

Figure 3:
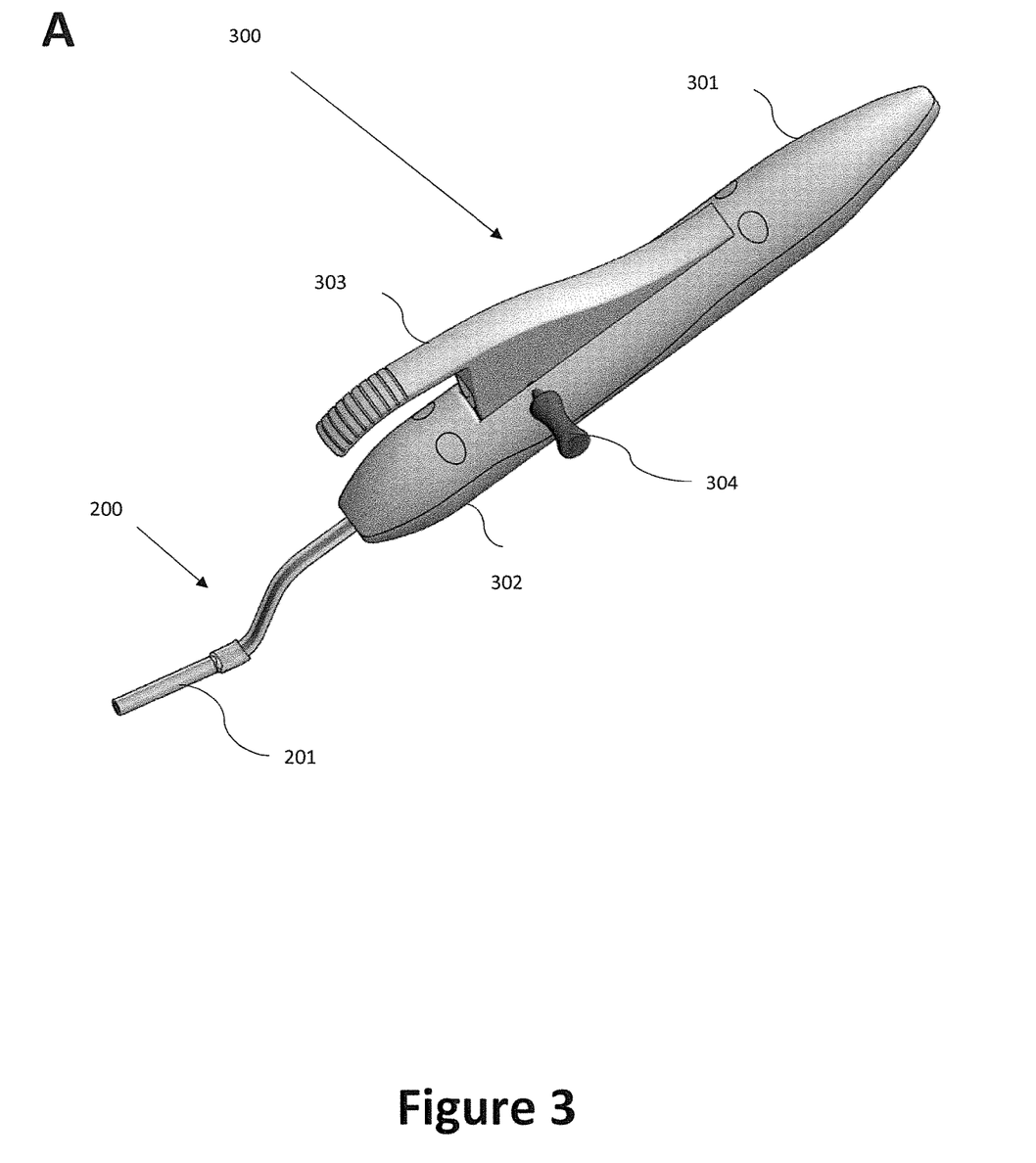
FIG. 3A shows a delivery device 300 with inserter attachment 200 and housing 301 comprising a handpiece 302, lever 303 and safety pin 304.
FIG. 3B shows delivery device in an un-actuated state. Implant 600 is retained in the lumen of tip 100.
FIG. 3C shows delivery device 300 in an actuated state. Internal sliding member 102 travels longitudinally along the lumen 104 of tip 100, pushing implant 600 out of opening 103 at the distal end of tip 100.

FIG. 3A shows delivery device 300 with inserter attachment 200 comprising a tip 100 and cap 201. Delivery device 300 comprises handpiece 301 with housing 302, lever 303 and safety pin 304. In its non-actuated state, implant 600 is held in place by flexible envelope 101 of tip 100 and resides its lumen 104 (FIG. 3B). Upon actuation of lever 303, internal sliding member 102 moves along the length of lumen 104, thereby deforming its dilatable cross-section. When engaging with implant 600, internal sliding member 102 pushes implant 600 in front of it through lumen 104. Eventually, implant 600 is released through opening 103 at the proximal end of tip 100.

Figure 4:
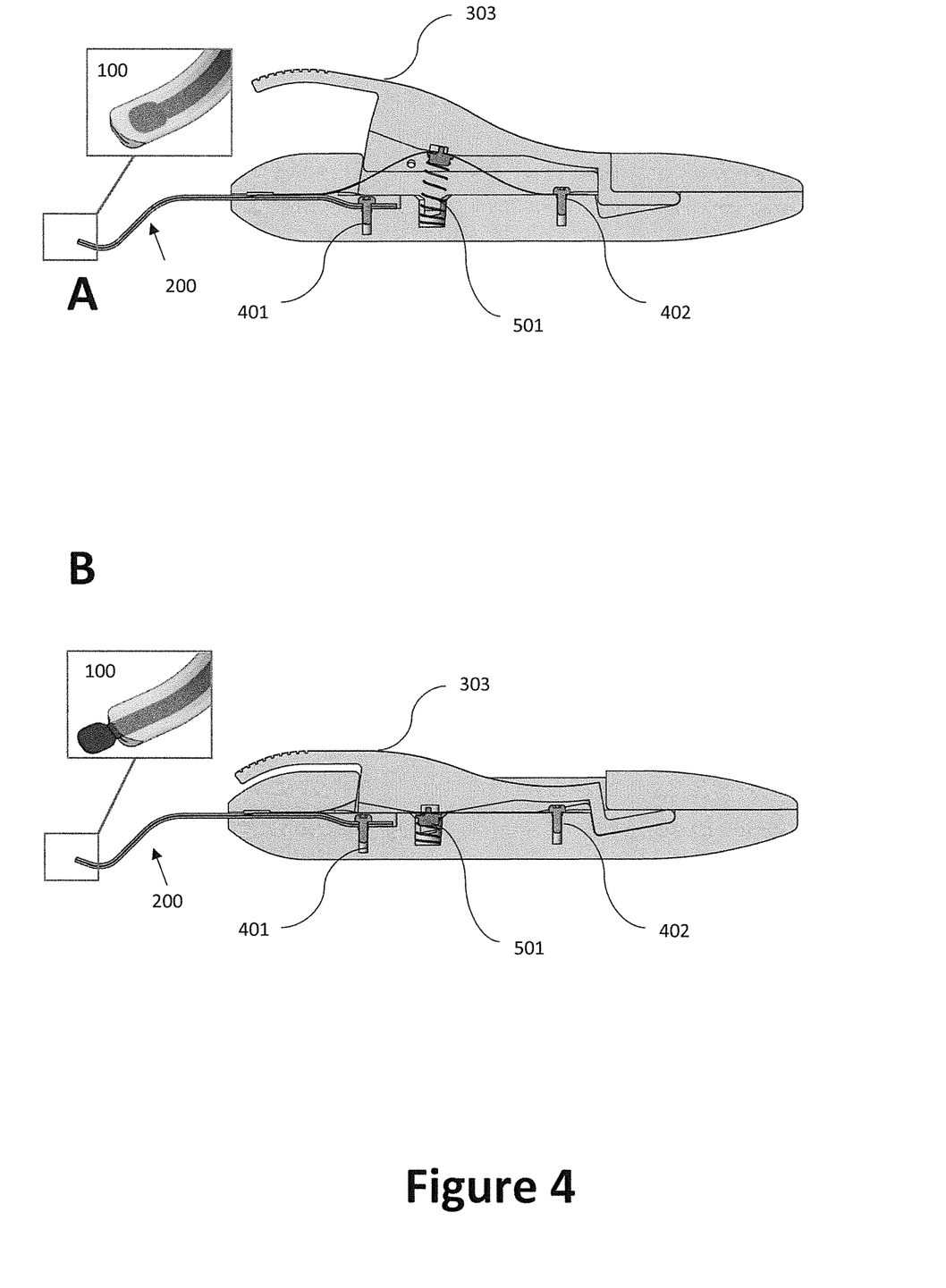
FIG. 4 illustrates actuation of the internal sliding member 102.

FIG. 4 shows the cross-section of delivery device 300 in its non-actuated (FIG. 4A) and actuated (FIG. 4B) state. Envelope 101 and internal sliding member 102 are affixed to housing 302 via suitable engagement means 401, 402.

Spring 501 serves as actuation means to translate the actuation of lever 303 to internal sliding member 102.

The present invention as described above may be of particular benefit when used to deploy retinal, especially epi- or sub-retinal, implants. In these cases, an incision (a sclerotomy) is made in the sclera of the eye and, in the case of a sub-retinal implant, an opening is also made in the retina (a retinotomy). Using an inserter attachment 200 coupled as described above to a handpiece 301, the tip 100, comprising the implant 600, is thereafter inserted through the sclerotomy and, in the case of a sub-retinal implant, optionally through the retinotomy. Once intraocularly inserted, the internal sliding member 102 may be controlled, as described above, to deposit the retinal implant 600 as desired. In this manner, a much greater degree of control is provided when implanting the retinal implant than was previously provided using prior art techniques.

Items

The present invention may preferably be characterized by the following items:

1. A tip 100 for a delivery device, comprising a flexible envelope 101, said envelope 101 defining a lumen 104.
2. The tip according to item 1, wherein said lumen 104 is characterized by a dilatable cross-section.
3. The tip according to item 1 or 2, wherein lumen 104 is capable of conforming to the dimensions of internal sliding member 102 passing through.
4. The tip according to any one of the preceding items, wherein said envelope 101 comprises or consists of at least one flexible and preferably biocompatible material.
5. The tip according to item 4, wherein said envelope material is selected from polytetrafluorethylene (PTFE); polyurethane, polyethylene, vinyl, expanded-polytetrafluoroethylene (ePTFE); silicone; or other materials.
6. The tip according to any one of the preceding items, wherein envelope 101 is transparent or translucent.
7. The tip according to any one of the preceding items, further comprising an internal sliding member 102 being movably disposed within the lumen 104.
8. The tip according to item 7, wherein said internal sliding member 102 is capable of moving in longitudinal direction along the length of the lumen 104.
9. The tip according to item 7 or 8, wherein said internal sliding member 102 comprises or consists of metal.
10. The tip according to any one of the preceding items, wherein said envelope 101 has a wall thickness of at least about 0.1 mm, 0.2 mm, 0.3 mm, 0.4 mm, 0.5 mm, 0.6 mm, 0.7 mm, 0.8 mm, 0.9 mm, 1.0 mm, preferably of about 0.5 mm.
11. The tip according to item any one of the preceding items, wherein lumen 104 is rounded or flattened or combinations thereof, optionally wherein the shape of lumen 104 varies along the length of the tip 100.
12. The tip according to any one of the preceding items, wherein said dilatable cross-section is chosen to retain implant 600 within lumen 104 when in an un-dilated state.
13. The tip according to item 12, wherein said dilatable cross-section falls below the dimensions of internal sliding member 102 when in an un-dilated state.
14. The tip according to any one of the preceding items, wherein said dilatable cross-section has a dilatable diameter; or a dilatable width and optionally a dilatable height.
15. The tip according to item 14, wherein said dilatable diameter or width essentially corresponds to the width of implant 600 when in an un-dilated state.
16. The tip according to item 14 or 15, wherein said dilatable diameter or width is at least about 1 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, preferably of between about 1.5 mm and 2.0 mm; and or wherein said dilatable height of at least about 0.1 mm, 0.2 mm, 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm or more.
17. The tip according to any one of the preceding items, wherein the dilatable cross-section can be dilated by at least 1%, 2%, 3%, 4%, 5%, 6%, 7%, 8%, 9%, 10%, 11%, 12%, 13%, 14%, 15%, 16%, 17%, 18%, 19%, 20% or more.
18. The tip according to any one of the preceding items, said tip having a shape configured for delivering an implant to a body site of interest, said tip preferably having a curved shape.
19. The tip according to any one of the preceding items, with its distal end being rounded or flattened and optionally tapered.
20. The tip according to any one of the preceding items, its distal end comprising an opening 103.
21. The tip according to any one of the preceding items, said tip 100 and preferably its distal end comprising rounded edges.
22. The tip according to any one of the preceding items, wherein said tip comprises an implant 600, preferably a retinal implant, retained in its lumen 104.
23. A cap for covering a tip 100 according to any one of items 1 to 22, preferably for sealing an opening 103 at the distal end of said tip.
24. The cap according to item 23, said cap comprising engagement means for detachably affixing said cap 201 to the tip 100.
25. An inserter attachment 200 for a delivery device, comprising the tip 100 according to any one of items 1 to 22; and optionally a cap 201 according to item 23 or 24 detachably mounted on said tip 100; and optionally engagement means for affixing said inserter attachment to a delivery device.
26. The inserter attachment according to item 25, wherein said cap 201 is configured to seal opening 103 at the distal end of tip 100.
27. The inserter attachment according to item 26, said inserter attachment being mounted on a delivery device 300 comprising: a handpiece 301, engagement means and actuation means.
28. Use of a tip 100 according to any one of items 1 to 22 or an inserter attachment according to any one of items 25 to 27 for assembling a delivery device.
29. An delivery device comprising: a handpiece 301 with a housing 302, engagement means and actuation means; and an inserter attachment 200 according to any one of items 25 to 27.
30. The delivery device according to item 29, wherein said engagement means are configured to allow the engagement/disengagement of the inserter attachment 200 to/from the handpiece 301.
31. The delivery device according to item 30, wherein said engagement means are capable of fixing envelope 101 and/or internal sliding member 102 to housing 302.
32. The delivery device according to any one of items 29 to 31, wherein the actuation means are configured to translate actuation from a lever 303 to the internal sliding member 102 of the inserter portion 200.
33. The delivery device according to item to any one of items 29 to 32, wherein said actuation means comprise a spring 501.

34. A method for manufacturing a tip according to any one of items 1 to 22 comprising providing an envelope according to any one of the preceding items; optionally providing an internal sliding member according to any one of the preceding items; and affixing said internal sliding member to said envelope.

35. A method for manufacturing or assembling a delivery device, comprising: (1) providing an inserter attachment 200 according to any one of items 25 to 27; (2) affixing said inserter attachment 200 to a handpiece 301.

36. The tip according to any one of item 1 to 22, wherein lumen 104 comprises an oval cross-sectional shape, preferably having two opposing pointed corners.

37. The tip according to any one of item 1 to 22 wherein lumen 104 comprises a cross-sectional shape comprising at least a first section having a first height and at least one other section having a second height smaller than the first height, wherein preferably, the a first section is adapted to provide a first cavity for receiving sliding member 102 and/or preferably the second section is adapted for holding, positioning and/or guiding implant 600.

38. The tip according to any one of item 1 to 22 or 36 to 37, being made in one piece.

39. The tip according to any one of item 1 to 22 or 36 to 37, comprising two or more parts which are assembled together, preferably comprising a distal region part preferably made of a polymer for receiving implant 600, and or more proximal parts may be provided adjacent to the distal region part in a proximal direction thereof.

40. The tip according to item 39, wherein the one or more proximal parts comprise the same material as the distal region part, or comprise a different material.

41. The tip according to item 39 or 40, wherein the one or more proximal parts comprise a different profile as the distal region part, wherein preferably the proximal is a flattened rigid tube, preferably comprising a metal material.

42. The tip according to any one of items 39 to 40, wherein the distal region part and the one or more proximal parts are assembled by an assembly method, preferably by gluing, welding, clipping, or press-fitting.

43. A method for manufacturing a tip according to any one of items 1 to 22 or 36 to 42, comprising providing an envelope according to any one of the preceding items; optionally providing an internal sliding member according to any one of the preceding items; and affixing said internal sliding member to said envelope.

44. The method for manufacturing a tip according to item 43, wherein envelope 101 is made from post-processing of a preferably circular tube, preferably a standard circular tube.

45. The method for manufacturing a tip according to item 44, wherein the tube being basis for the envelope is pressed, preferably to a predetermined height preferably such that a cross-sectional shape of a lumen of the tube adapts to a predetermined cross-sectional shape of lumen 104.

46. The method for manufacturing a tip according to item 44 or 45, wherein pressing of the tube is performed at room temperature or at an elevated temperature.

47. The method for manufacturing a tip according any one of items 44 to 46, wherein the tube comprises a polymer material, wherein the elevated temperature is higher than a glass transition temperature of the polymer material.

48. The method for manufacturing a tip according to item 47, wherein the temperature applied to the tube is lowered again, preferably below the glass transition temperature, particularly preferably to room temperature, before pressing of the tube is released.

49. The method for manufacturing a tip according to any one of items 43 to 48, wherein a mandrel is inserted into the tube before pressing and wherein the mandrel is being kept inside the tube during the step of pressing the tube.

50. The method for manufacturing a tip according to item 43, wherein the envelope is formed in an extruding step.

51. The method for manufacturing a tip according to item 43, wherein the envelope is formed by overmolding a suitable material around a mandrel, wherein wherein preferably the mandrel comprises a cross-sectional shape corresponding to a predetermined cross-sectional shape of lumen 104.

52. The method for manufacturing a tip according to item 43, wherein envelope 101 is formed by a heat shrink step, preferably, by forming a heat shrink tube around a mandrel, wherein preferably the mandrel comprises a cross-sectional shape corresponding to a predetermined cross-sectional shape of lumen 104.

The invention claimed is:

1. A delivery device comprising:
a hand piece with a housing, engagement means, and actuation means; and
an inserter attachment comprising a tip, wherein the tip comprises a flexible envelope, said envelope defining a lumen, and further comprises an internal sliding member being moveably disposed within the lumen, wherein the internal sliding member is capable of moving in longitudinal direction along the length of the lumen, and wherein a spring serves as an actuation means to translate the actuation of a lever to the internal sliding member.

2. The delivery device according to claim 1, wherein said delivery device is configured to deliver implants, including retinal implants, to a body site of interest.

3. The delivery device according to claim 1, wherein the lumen having dilatable cross-section, said dilatable cross-section chosen to retain an implant within said lumen when in an un-dilated state.

4. The delivery device according to claim 1, wherein said internal sliding member comprises metal.

5. The delivery device according to claim 1, wherein said lumen is configured to conform to dimensions of the internal sliding member passing through.

6. The delivery device according to claim 1, wherein the envelope:
(1) comprises at least one flexible and biocompatible material
(2) is transparent or translucent; and/or
(3) has a wall thickness of at least about 0.1 mm, 0.2 mm, 0.3 mm, 0.4 mm, 0.5 mm, 0.6 mm, 0.7 mm, 0.8 mm, 0.9 mm, or 1.0 mm.

7. The delivery device according to claim 3, wherein said dilatable cross-section has a dilatable diameter or width of at least about 1 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, or 3.0 mm, or between about 1.5 mm and 2.0 mm; and/or a dilatable height of at least about 0.1 mm, 0.2 mm, 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, or 1.5 mm or more.

8. The delivery device according to claim 3, wherein the dilatable cross-section can be dilated by at least 1%, 2%, 3%, 4%, 5%, 6%, 7%, 8%, 9%, 10%, 11%, 12%, 13%, 14%, 15%, 16%, 17%, 18%, 19%, or 20% or more.

9. The delivery device according to claim 1, said tip having a shape configured for delivering an implant to a body site of interest, said tip having a curved shape.

10. The delivery device according to claim 1, wherein the tip comprises an opening at a distal end.

11. The delivery device according to claim 1, wherein the lumen comprises an oval cross-sectional shape.

12. The delivery device according to claim 1, wherein the lumen comprises a cross-sectional shape comprising at least a first section having a first height and at least one other section having a second height smaller than the first height, wherein the first section is adapted to provide a first cavity for receiving a sliding member and/or the second section is adapted for holding, positioning and/or guiding an implant.

13. The delivery device according to claim 1, further comprising a cap detachably affixed to said tip.

14. The delivery device according to claim 13, wherein the cap is configured for sealing an opening at a distal end of said tip.

15. The delivery device according to claim 11, wherein the oval cross-sectional shape has two opposing pointed corners.

16. The delivery device according to claim 6, wherein the at least one flexible and biocompatible material, is selected from polytetrafluorethylene (PTFE); polyurethane, polyethylene, vinyl, expanded-polytetrafluoroethylene (ePTFE); silicone; or other materials.

* * * * *